(12) United States Patent
Shigemori et al.

(10) Patent No.: US 10,570,372 B2
(45) Date of Patent: Feb. 25, 2020

(54) METHOD FOR MANUFACTURING PLATELETS BY ROTARY STIRRING CULTURE METHOD

(71) Applicant: Megakaryon Corporation, Kyoto (JP)

(72) Inventors: Tomohiro Shigemori, Kyoto (JP); Haruki Okamoto, Kyoto (JP)

(73) Assignee: Megakaryon Corporation, Kyoto (JP)

( * ) Notice: Subject to any disclaimer, the term of this patent is extended or adjusted under 35 U.S.C. 154(b) by 0 days.

(21) Appl. No.: 15/759,634

(22) PCT Filed: Sep. 8, 2016

(86) PCT No.: PCT/JP2016/076406
§ 371 (c)(1),
(2) Date: Mar. 13, 2018

(87) PCT Pub. No.: WO2017/047492
PCT Pub. Date: Mar. 23, 2017

(65) Prior Publication Data
US 2018/0258395 A1   Sep. 13, 2018

(30) Foreign Application Priority Data

Sep. 15, 2015   (JP) .................. 2015-182221

(51) Int. Cl.
*C12N 5/078* (2010.01)
*A61K 35/14* (2015.01)
*A61K 35/19* (2015.01)

(52) U.S. Cl.
CPC ............ *C12N 5/0644* (2013.01); *A61K 35/14* (2013.01); *A61K 35/19* (2013.01); *C12N 2506/13* (2013.01); *C12N 2527/00* (2013.01)

(58) Field of Classification Search
None
See application file for complete search history.

(56) References Cited

U.S. PATENT DOCUMENTS

| 2011/0053267 A1 | 3/2011 | Nakauchi et al. |
| 2011/0065190 A1 | 3/2011 | Nakano et al. |
| 2012/0014933 A1 | 1/2012 | Baruch et al. |
| 2014/0127815 A1 | 5/2014 | Eto et al. |
| 2016/0002599 A1 | 1/2016 | Eto |

FOREIGN PATENT DOCUMENTS

| JP | 2009-297023 A | 12/2009 |
| JP | 2012-510804 A | 5/2012 |
| WO | 2009122747 A1 | 10/2009 |
| WO | 2011009625 A1 | 1/2011 |
| WO | 2012157586 A1 | 11/2012 |
| WO | 2014100779 A1 | 6/2014 |
| WO | 2014123242 A1 | 8/2014 |

OTHER PUBLICATIONS

Feng, et al., "Scalable Generation of Universal Platelets from Human Induced Pluripotent Stem Cells", Nov. 11, 2014, pp. 817-831, vol. 3, Publisher: Stem Cell Reports.
Harimoto, et al., "Towards Industrialization: Development of Ips cell-derived Platelet Production System", Sep. 1, 2015, pp. S-15, vol. 21, No. Suppl. 1, Publisher: Tissue Engineering Part A.
Nakamura, et al., "Expandable Megakaryocyte Cell Lines Enable Clinically Applicable Generation of Platelets from Human Induced Pluripotent Stem Cells", Apr. 1, 2014, pp. 535-548, vol. 14, No. 4, Publisher: Cell Stem Cell.
International Search Report received in PCT/JP2016/076406 dated Nov. 15, 2016.
Written Opinion received in PCT/JP2016/076406 dated Nov. 15, 2016.
Junt, et al., "Dynamic visualization of thrombopoiesis within bone marrow", Sep. 21, 2007, pp. 1767-70, vol. 317, No. 5845, Publisher: Science.
Nakagawa, et al., "Two differential flows in a bioreactor promoted platelet generation from human pluripotent stem cell-derived megakaryocytes", Apr. 22, 2012, pp. 742-8, vol. 41, No. 8, Publisher: Exp Hematol.
Thon, et al., "Platelet bioreactor-on-a-chip", Sep. 18, 2014, pp. 1857-67, vol. 124, No. 12, Publisher: Blood.

*Primary Examiner* — Blaine Lankford
(74) *Attorney, Agent, or Firm* — Suzannah K. Sundby, Esq.; Canady + Lortz LLP (57) ABSTRACT

The present invention provides a method for producing platelets, and the method comprises a step of culturing megakaryocytes in a culture solution in a culture vessel, wherein the culture solution is stirred with a stirrer in the culture step.

7 Claims, 5 Drawing Sheets

UNUSUAL PLATELETS

BCP

FLASK

Fig. 5

METHOD FOR MANUFACTURING PLATELETS BY ROTARY STIRRING CULTURE METHOD

TECHNICAL FIELD

The present invention relates to a method for manufacturing platelets by a rotary stirring culture method.

BACKGROUND ART

Platelet preparations are administered for the purpose of treating and preventing the symptoms of patients experiencing heavy bleeding during surgery or injury, or patients exhibiting a bleeding tendency associated with decreased platelets following anticancer drug treatment. At present, production of platelet preparations relies on blood donations from healthy volunteers. However, the number of blood donors in Japan is decreasing for demographic reasons, and it is estimated that by 2027 there will be a shortage of about a million donors. Therefore, securing a stable supply of platelets is an objective in the technical field of the present invention.

Moreover, because conventional platelet preparations are at high risk of bacterial contamination, there is a danger of serious infections occurring after transplantation of platelet preparations. Therefore, there is always a clinical demand for safer platelet preparations. To meet this demand, methods are now being developed for producing platelets from megakaryocytes cultured in vitro.

Conventionally, production of platelets from cultured cells has been performed in a stationary culture system using a dish (WO 2014/100779A1, Qiang Feng et al., Stem Cell Reports). However, stationary culture systems are extremely labor-intensive and have not been suited to large-scale culture.

CITATION LIST

Patent Document

Patent Document 1: WO 2014/100791

Non-Patent Document

Non-Patent Document 1: Qiang Feng et al., Stem Cell Reports 3, 1-15 (2014)

SUMMARY

Technical Problem

The present inventors succeeded in producing platelets with high bioactivity in a shaking culture system using a shaker flask, i.e., a culture method in which the culture vessel itself is shaken. However, it was found that in a shaker flask culture system, the amount of (CD41a+CD42b+) platelets produced and the platelet bioactivity (PAC1 binding, P-selectin positive rate) are reduced as the amount of the medium is scaled up.

A platelet degradation (CD42b positive rate reductions), which can be attributed to shedding and the like, was also found to occur in the shaker flask culture system. Moreover, it was found that such a system contains more unusual platelets (Annexin V-positive platelets), which are unsuited to in vivo transplantation.

It is therefore an object of the present invention to provide a method for large-scale production of high-quality platelets that can be transplanted in vivo.

Solution to Problem

As a result of extensive research aimed at solving the above-mentioned problems, the inventors found that culturing megakaryocytes while stirring the culture solution in a rotating direction with a stirrer disposed in the culture vessel, rather than by shaking the culture vessel, can increase the production efficiency and bioactivity of platelets, control platelet degradation at a low level and reduce unusual platelets. The present invention was completed after further research into the culture conditions including the cell density during culture by stirring culture, the stirring rotation speed and the like.

That is, the present invention is a method for producing platelets, comprising a step of culturing megakaryocytes in a culture solution in a culture vessel, wherein the culture solution is stirred with a stirrer in the culture step.

In the method for producing platelets of the present invention, the stirrer preferably has a blade shape.

In the method for producing platelets of the present invention, the culture vessel is preferably a sealed bioreactor.

In the method for producing platelets of the present invention, the stirrer is preferably rotated at a rotational speed of at least 50 rpm.

Moreover, in the method for producing platelets of the present invention, the megakaryocytes are preferably cells obtained by overexpressing at least one gene selected from the group consisting of a cancer gene, a polycomb gene and an apoptosis suppression gene in undifferentiated cells of megakaryocytes, and then terminating the overexpression.

The present invention is also a method for producing a platelet preparation, comprising: a step of producing platelets in megakaryocytes by the methods described above and collecting the platelets from a culture; and a step of removing blood cell components other than platelets from the platelets.

The present invention also provides a method for producing a blood preparation, compirising: a step of producing a platelet preparation by the methods described above; and a step of mixing this platelet preparation with other components to obtain a blood preparation.

The present invention also provides platelets manufactured by any of the methods above.

The present invention also provides a platelet preparation manufactured by any of the methods above, or a platelet preparation containing the above-described platelets.

The present invention also provides a blood preparation produced by the methods above, or a blood preparation containing the above-described platelets.

Advantageous Effects of Invention

With the method of the present invention, it is possible to improve platelet production efficiency over that obtained with a conventional shaking culture. Moreover, the resulting platelets have bioactivity exceeding that of platelets produced with a conventional shaking culture.

Moreover, with the method of the present invention it is possible to suppress a platelet degradation reaction (CD42b positive rate reduction), and also suppress production of unusual platelets (Annexin V-positive platelets).

DESCRIPTION OF EMBODIMENTS

The method for producing platelets of the present invention comprises a step of culturing megakaryocytes in a culture solution in a culture vessel, wherein the culture solution is stirred with a stirrer in a rotational direction in the culture step.

In this Description, the "culture vessel" is not particularly limited as long as it is a vessel in which megakaryocytes can be cultured as the culture solution is stirred with a stirrer, and examples include closed-system screw cap flasks, bioreactors and the like.

In this Description, the "stirrer" may be any capable of directly stirring a culture solution when disposed in the culture solution, and examples include various kinds of stir bars used in magnetic stirrers, and stirring blades attached to bioreactors. When using the stir bar of a magnetic stirrer, the stir bar is placed in the culture solution, and the culture solution can then be stirred by rotating the magnet with a motor from outside the culture vessel. In the case of a bioreactor with a stirring blade, a blade inside the bioreactor is disposed below the liquid surface of the culture solution, and the stirring blade can then be rotated by a motor attached to the bioreactor to thereby stir the culture solution.

An example using a bioreactor with a stirring blade is explained below as one embodiment of the invention.

In this Description, a "bioreactor" may be any having a culture tank capable of culturing megakaryocytes and a stirring mechanism capable of stirring a culture solution inside the culture tank, and a commercial bioreactor may be used.

The bioreactor provides a physiochemical environment suited to optimal cell proliferation, cell metabolism, differentiation and maturation of megakaryocytes, multinucleation of megakaryocytes, proplatelet formation, platelet production, maintenance of platelet bioactivity and the like. Consequently, it may be equipped with an aeration mechanism, exhaust mechanism, temperature control mechanism, pH control mechanism, dissolved oxygen tension (DOT) regulation mechanism, baffle, sparger, port and the like.

The stirring mechanism of the bioreactor may be configured in any way that allows it to stir the culture solution, and for example it may be configured with an impeller attached inside the culture tank and driven by a motor, together with a stirring blade fixed to the impeller.

When stirring the bioreactor in the present invention, the stirring rotation speed is not particularly limited, but may be 10 rpm to 300 rpm, or preferably at least 50 rpm for example. More preferably it is at least 100 rpm, or still more preferably at least 140 rpm.

The shape of the culture tank of the bioreactor is also not particularly limited, and may be for example a vertical tube shape, or a shape with flat surfaces at the top and bottom of the tank.

The culture tank has a volume of at least 0.3 liters, or preferably at least 1 liter, or 50 liters, or more preferably at least 200 liters, or still more preferably at least 500 liters, or yet more preferably at least 1000 liters, or most preferably at least 2000 liters.

The shape of the blade of the bioreactor in the present invention is not limited. For example, a flat-bladed turbine type, propeller type, arrowhead blade type, curved blade type or one plane bladed disk turbine type may be used.

In the present Description, "megakaryocytes" are the largest cells present in bone marrow in vivo, and have the property of releasing platelets. They also have the property of being positive for the cell surface markers CD41a, CD42a and CD42b, and may also express markers selected from the group consisting of CD9, CD61, CD62p, CD42c, CD42d, CD49f, CD51, CD110, CD123, CD131 and CD203c. When "megakaryocytes" are multinucleated (polyploidized), they have 16 to 32 times as much genome DNA as normal cells, but in this Description the term "megakaryocyte" by itself encompasses both multinucleated megakaryocytes and megakaryocytes before multinucleation, as long as the aforementioned properties are present. "Megakaryocytes before multinucleation" may also be called "immature megakaryocytes" or "growth stage megakaryocytes".

Megakaryocytes can be obtained by various known methods. Non-limiting examples of methods for producing megakaryocytes include the method described in WO 2011/034073. In this method, an immortalized megakaryocytic progenitor cell line that proliferates indefinitely can be obtained by overexpressing a cancer gene and a polycomb gene in "undifferentiated cells of megakaryocytes". Moreover, following the methods described in WO 2012/157586, immortalized megakaryocytes can also be obtained by overexpressing an apoptosis suppression gene in "undifferentiated cells of megakaryocytes". When these immortalized megakaryocytes are released from forced gene expression, multinucleation progresses and the platelets are released.

The methods described in the aforementioned literature may also be combined to obtained megakaryocytes. In this case, overexpression of a cancer gene, a polycomb gene and an apoptosis suppression gene can be performed either simultaneously or sequentially. For example, the cancer gene and polycomb gene can be overexpressed, and this overexpression can then be suppressed, after which the apoptosis suppression gene is overexpressed and that overexpression is suppressed to obtain multinucleated megakaryocytes. Alternatively, the cancer gene, polycomb gene and apoptosis suppression gene can be overexpressed simultaneously, after which this overexpression is simultaneously suppressed to obtain multinucleated megakaryocytes. The cancer gene and polycomb gene can also be overexpressed first, after which the apoptosis suppression gene is overexpressed, and all of the overexpression is then simultaneously suppressed to obtain multinucleated megakaryocytes.

In this Description, "undifferentiated cells of megakaryocytes" are cells having the ability to differentiate into megakaryocytes, and may be cells at various differentiation stages leading from hematopoietic stem cell lines to megakaryocytes. Non-limiting examples of undifferentiated cells of megakaryocytes include hematopoietic stem cells, hematopoietic progenitor cells, CD34-positive cells and megakaryocyte-erythroid progenitor (MEP) cells. These cells may be obtained by isolating cells from bone marrow, umbilical cord blood or peripheral blood, or by differentiation induction from pluripotent stem cells such as ES cells or iPS cells, which are more undifferentiated cells.

In this Description, a "cancer gene" is a gene that induces cancerization of cells in vivo, and examples include MYC family genes (such as c-MYC, N-MYC and L-MYC), SRC family genes, RAS family genes, RAF family genes, and c-Kit, PDGFR, Abl and other protein kinase family genes.

In this Description, "polycomb genes" are genes that negatively control CDKN2a (INK4a/ARF) genes, and are known as genes that function to prevent cell aging (Ogura et al, Saisei Iryo (Regenerative Medicine) Vol. 6, No. 4, pp. 26-32; Jseus et al, Natural Reviews Molecular Cell Biology Vol. 7, pp. 667-677, 2006; Proc. Natl. Acad. Sci. USA, Vol. 100, pp. 211-216, 2003). Non-limiting examples of polycomb genes include BMI1, Me118, Ringla/b, Phc1/2/3, Cbx2/4/6/7/8, Ezh2, Eed, Suz12, HADC and Dnmt1/3a/3b.

In this Description, an "apoptosis suppression gene" is a gene having the function of suppressing cell apoptosis, and examples include the BCL2 gene, BCL-xL gene, Survivin gene, MCL1 gene and the like.

Forced gene expression and termination of overexpression may be accomplished by the methods described in WO 2011/034073, WO 2012/157586, WO 2014/123242 or in Nakamura S. et al., Cell Stem Cell 14, 535-548, 2014, or by other known methods.

In this Description, "platelets" are a cell component of blood, and have the properties of being CD41a positive and CD42b positive. Platelets play a vital role in thrombus formation and hemostasis, and are also involved in tissue regeneration after injury and in the pathophysiology of inflammation. When platelets are activated by bleeding or the like, the receptors of cell adhesion factors such as Integrin αIIBβ3 (glycoprotein IIb/IIIa; complex of CD41a and CD61) are expressed on their cell membranes. The platelets aggregate together as a result, and fibrin is coagulated by the various blood clotting factors released by the platelets, leading to thrombus formation and hemostasis.

The functions of platelets can be measured and evaluated by known methods. For example, the quantity of activated platelets can be measured using antibodies to PAC-1, which binds specifically to Integrin αIIBβ3 on the cell membranes of the activated platelets. The quantity of activated platelets can also be measured by using antibodies to detect the platelet activation marker CD62P (P-selectin). For example, gating can first be performed by flow cytometry using antibodies to the activation-independent platelet marker CD61 or CD41, and binding by anti-PAC-1 antibodies or anti-CD62P antibodies can then be detected. These steps may be performed in the presence of adenosine diphosphate (ADP).

Platelet function can also be evaluated by looking at whether binding with fibrinogen occurs in the presence of ADP. Binding of platelets with fibrinogen results in the activation of integrins necessary for the early stages of thrombus formation.

Platelet function can also be evaluated by a method for imaging and observing thrombus formation ability in vivo, as shown in FIG. 6 of WO 2011/034073.

When platelets have a low CD42b expression rate or a low Annexin V positive rate, on the other hand, the platelets are considered to be degraded or unusual. These platelets are not clinically useful because they do not have sufficient thrombus formation or hemostatic function.

In this Description, "platelet degradation" means that CD42b (GPIba) is reduced on the platelet surfaces. Consequently, degraded platelets comprise platelets with reduced CD42b expression, and platelets from which the CD42b extracellular regions have been excised through shedding. Once CD42b has been removed from the platelet surfaces, the blood clotting function of the platelets is lost because they are no longer capable of conjoining with von Willebrand factor (VWF). Platelet degradation can be evaluated based on the CD42b negative rate (or number of CD42b-negative particles) relative to the CD42b positive rate (or number of CD42b-positive particles). The higher the CD42b negative rate relative to the CD42b positive rate, or the greater the number of CD42b negative particles relative to the number of CD42b positive particles, the greater the platelet degradation. The CD42b positive rate is the percentage of platelets capable of binding to anti-CD42b antibodies out of the platelets contained in a platelet fraction, and the CD42b negative rate is the ratio of platelets that do not bind to anti-CD42b antibodies out of the platelets contained in a platelet fraction.

In this Description, "unusual platelets" are platelets in which the negatively charged phospholipid phosphatidylserine is exposed from the inside to the outside of the lipid bilayer. In vivo, phosphatidylserine is exposed on the cell surface when platelets are activated, and binds there with many blood-clotting factors to enhance blood clotting cascade reactions. In unusual platelets, on the other hand, large amounts of phosphatidylserine are always exposed on the cell surfaces, and when such platelets are administered to patients they may cause excessive blood clotting reactions and lead to serious conditions such as disseminated intravascular coagulation syndrome. Since Annexin V binds to phosphatidylserine, phosphatidylserine on platelet surfaces can be detected by flow cytometry based on the amount of binding of fluorescent-labeled Annexin V. Consequently, the quantity of unusual platelets can be evaluated based on the Annexin V positive rate of a platelet fraction, or in other words based on the ratio or number of platelets exhibiting Annexin binding. The higher the Annexin V positive rate or the greater the number of Annexin V particles, the greater the number of unusual platelets.

The conditions for culturing the megakaryocytes in the present invention may be ordinary conditions. For example, the temperature may be about 35° C. to 42° C., or 36° C. to 40° C., or 37° C. to 39° C., and 5% to 15% $CO_2$ and/or 20% $O_2$ may be used.

The medium for culturing the megakaryocytes is not particularly limited, and a known medium suited to producing platelets from megakaryocytes or an equivalent medium may be used appropriately. For example, the medium may be prepared using a medium used for culturing animal cells as the basal medium. Examples of the basal medium include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal medium (Life Technologies Corporation), and mixtures of these.

The medium may contain serum or plasma, or may be serum free. The medium may also contain one or more substances such as albumin, insulin, transferrin, serine, fatty acids, trace elements, 2-mercaptoethanol, thiolglycerol, monothioglycerol (MTG), lipids, amino acids (such as L-glutamine), ascorbic acid, heparin, non-essential amino acids, vitamins, growth factors, low-molecular-weight compounds, antibiotics, antioxidants, pyruvic acid, buffers, inorganic salts, cytokines and the like as necessary. Cytokines are proteins that promote blood cell differentiation, and examples include vascular endothelial growth factor (VEGF), thrombopoietin (TPO), various TPO-like active substances, stem cell factor (SCF), ITS (insulin-transferrin-selenite) supplement, ADAM inhibitors and the like. In the present invention, a preferred medium is IMDM medium containing serum, insulin, transferrin, serine, thiolglycerol, ascorbic acid and TPO. It may also contain SCF, and may also contain heparin. The various concentrations of these are not particularly limited, but for example the concentration of TPO may be about 10 ng/mL to 200 ng/mL, or about 50 ng/mL to about 100 ng/mL, while that of SCF may be about 10 ng/mL to 200 ng/mL, or about 50 ng/mL, and that of heparin may be about 10 U/mL to 100 U/mL, or about 25 U/mL. A phorbol ester (such as phorbol-12-myristate-13-acetate (PMA)) may also be added.

When serum is used, human serum is preferred. Human plasma or the like may also be used in place of serum. With the method of the present invention, platelets equivalent to those obtained using serum can also be obtained using these components.

When a drug-responsive gene expression induction system such as Tet-On™ or Tet-off™ is used to induce and terminate overexpression of gene, the corresponding drug, such as tetracycline or doxycycline, may be contained in the medium in the overexpression step, and overexpression can then be suppressed by excluding these from the medium.

The megakaryocyte culture step in the present invention may be accomplished without feeder cells if it is performed as a floating culture.

The present invention encompasses platelets manufactured by the method of the present invention.

The method for producing a platelet preparation of the present invention comprises a step of culturing megakaryocytes by the method of the invention to produce platelets and collecting a platelet-rich fraction from the culture, and a step of removing blood cell components other than platelets from the resulting platelet fraction. The step of removing the blood cell components may be performed by using a leukocyte removal filter (manufactured by Terumo Corporation or Asahi Kasei Medical Co., Ltd. for example) or the like to remove blood cell components other than platelets, including megakaryocytes. More specific methods of manufacturing platelet preparations are described for example in WO 2011/034073.

The method for producing a blood preparation of the present invention comprises a step of producing a platelet preparation by the methods of the present invention, and a step of mixing this platelet preparation with other components. Examples of the other components include red blood cells for example.

Other components that contribute to cell stabilization may also be added to the platelet preparation and blood preparation.

The entire disclosures of all of the patent documents and non-patent documents cited in this Description are incorporated by reference in this Description.

Example 1

The present invention is explained in detail below based on examples, but the present invention is in no way limited to these. A person skilled in the art may modify the present invention in various ways without deviating from the meaning of the present invention, and such modifications are also included in the scope of the present invention.

1. Preparation of Immortalized Megakaryocytes 1-1. Preparation of Hematopoietic Progenitor Cells from iPS Cells A differentiation culture was performed to differentiate human iPS cells (TKDN SeV2: iPS cells from human fetal skin fibroblasts established using Sendai virus) into blood cells by the methods described in Takayama N. et al., J. Exp. Med. 2817-2830 (2010). That is, a human ES/iPS cell colony was co-cultured for 14 days with C3H10T1/2 feeder cells in the presence of 20 ng/mL VEGF (R&D Systems, Inc.) to prepare hematopoietic progenitor cells (HPC). The culture conditions were 20% $O_2$, 5% $CO_2$ (here and below unless otherwise specified).

1-2. Gene Introduction system

A lentiviral vector system was used as the gene introduction system. The lentiviral vector is a tetracycline-controlled Tet-On™ gene expression induction system vector. c-MYC, BMI1, and BCL-xL were substituted for the mOKS cassette of LV-TRE-mOKS-Ubc-tTA-I2G (Kobayashi, T. et al., Cell 142, 787-799 (2010)) mOKS to prepare LV-TRE-c-Myc-Ubc-tTA-I2G, LV-TRE-BMI1-Ubc-tTA-I2G and LV-TRE-BCL-xL-Ubc-tTA-I2G, respectively.

Viral particles were prepared by genetically introducing the aforementioned lentiviral vectors into 293T cells.

Infecting target cells with these viral vectors serves to introduce the BMI1, MYC and BCL-xL genes into the genome sequences of the target cells. Once these genes have been stably introduced into a genome sequence, they can be overexpressed by adding doxycycline (#631311 (Clontech Laboratories, Inc.)) to the medium.

1-3. c-MYC and BMI1 Virus Infection of Hematopoietic Progenitor Cells

HPC cells obtained by the methods described above were seeded $5 \times 10^4$ cells/well on 6-well plates that had been previously seeded with C3H10T1/2 feeder cells, and c-MYC and BMI1 were overexpressed by the lentiviral method. 6 wells were used per each cell line. That is, viral particles were added to the medium at a ratio of MOI 20 for each, and infected by spin infection (32° C., 900 rpm, 60 minutes centrifugation). This operation was performed twice at an interval of 12 hours.

The medium used was basic medium (IMDM (Iscove's Modified Dulbecco's Medium) (Sigma-Aldrich Company Ltd.) containing 15% fetal bovine serum (Gibco), 1% penicillin-streptomycin-glutamine (Gibco), 1% insulin-transferrin-selenium solution (ITS-G, Gibco), 0.45 mM 1-thioglycerol (Sigma-Aldrich Company Ltd.) and 50 μg/mL L-ascorbic acid (Sigma-Aldrich Company Ltd.)) with 50 ng/mL human thrombopoietin (TPO, R&D Systems, Inc.), 50 ng/mL human stem cell factor (SCF, R&D Systems, Inc.) and 2 μg/mL doxycycline (Dox) added thereto (hereunder called differentiation medium), to which protamine was further added to a final concentration of 10 μg/mL.

1-4. Preparation and Maintenance Culture of Self-Propagating Megakaryocytic Cell Lines With infection day 0 as the day on which cMYC and BMI1 viral infection was performed by the methods described above, the megakaryocytes with the introduced cMYC and BMI1 genes were cultured to prepare self-propagating megakaryocytic cell lines for each. Overexpression of the BMI1 gene and c-MYC gene was achieved by adding 1 μg/mL of doxycycline (#631311 (Clontech Laboratories, Inc.)) to the medium.

Infection Day 2 to Infection Day 11

The virally infected blood cells obtained by the methods described above were collected by pipetting and centrifuged for 5 minutes at 1200 rpm, the supernatant was removed, and the cells were suspended in new differentiation medium and seeded on C3H10T1/2 feeder cells (6-well plate). On infection day 9 the cells were passaged by the same operations. The cells were counted and seeded on C3H10T1/2 feeder cells (6-well plate) at $1\times10^5$ cells/2 mL/well.

Infection Day 12 to Infection Day 13

The same operations were performed as on infection day 2. The cells were counted and then seeded on C3H10T1/2 feeder cells (100 mm dish) at $3\times10^5$ cells/10 mL/100 mm dish.

Infection Day 14

The virally infected blood cells were collected, and subjected to antibody reactions using 2 μL of anti-human CD41a-APC antibodies (BioLegend, Inc.), 1 μL of anti-human CD42b-PE antibodies (eBioscience) and 1 μL of anti-human CD235ab-Pacific Blue antibodies (BioLegend, Inc.) per $1.0\times10^5$ cells. Following the reaction, these were analyzed with FACSVerse (Becton, Dickinson and Company). On infection day 14, cells with a CD41a-positive rate of at least 50% were taken as a self-propagating megakaryocytic cell line.

1-4. BCL-xL Virus Infection of Self-Propagating Megakaryocytic Cell Lines

BCL-xL was genetically introduced by the lentivirus method into the previous self-propagating megakaryocytic cell line from infection day 14. The viral particles were added to the medium to a ratio of MOI 10, and infected by spin infection (32° C., 900 rpm, 60 minutes centrifugation). Overexpression of the BCL-xL gene was accomplished by adding 1 μg/mL of doxycycline (#631311 (Clontech Laboratories, Inc.)) to the medium.

1-5. Preparation and Maintenance Culture of Immortalized Megakaryocyte Line

Infection Day 14 to Infection Day 18

The self-propagating megakaryocytic cell line with the introduced BCL-xL gene obtained by the methods described above was collected and centrifuged for 5 minutes at 1200 rpm. Following centrifugation, the precipitated cells were suspended in new differentiation medium, and seeded to $2\times10^5$ cells/2 mL/well on new C3H10T1/2 feeder cells (6-well plate).

Infection Day 18: Passage

The cells were counted, and seeded at $3\times10^5$ cells/10 mL/100 mm dish.

Infection Day 24: Passage

The cells were counted, and seeded at $1\times10^5$ cells/10 mL/100 mm dish. These were subsequently passaged every 4 to 7 days to perform maintenance culture.

On infection day 24, the self-propagating megakaryocytic cell line with the introduced BCL-xL gene was collected, immune stained using 2 μL of anti-human CD41a-APC antibodies (BioLegend, Inc.), 1 μL of anti-human CD42b-PE antibodies (eBioscience) and 1 μL of anti-human CD235ab-Pacific Blue antibodies (Anti-CD235ab-PB, BioLegend, Inc.) per $1.0\times10^5$ cells, and analyzed with FACSVerse (Becton, Dickinson and Company), and also on infection day 24 a line having a CD41a-positive rate of at least 50% was taken as an immortalized megakaryocyte line. These cells, which had propagated successfully for at least 24 days after infection, were designated the immortalized megakaryocyte line SeV2-MKCL.

The resulting SeV2-MKCL was stationary cultured on a 10 cm dish (10 mL/dish). The medium was IMDM basic medium, to which the following components were added (final concentrations given).

| | |
|---|---|
| FBS (#172012 lot. 12E261 (Sigma)) | 15% |
| L-Glutamine (#25030-081 (Gibco)) | 2 mM |
| ITS (#41400-045 (Gibco)) | 100x dilution |
| MTG (monothioglycerol, #M6145-25ML (Sigma)) | 450 μM |
| Ascorbic acid (#A4544 (Sigma)) | 50 μg/mL |
| Puromycin (#P8833-100MG (Sigma)) | 2 μg/mL |
| SCF (#193-15513 (Wako Pure Chemical Industries, Ltd)) | 50 ng/mL |
| TPO-like active substance | 200 ng/mL |
| The culture conditions were 37° C., 5% $CO_2$. | |

2. Platelet Production

Overexpression was then removed by culturing the cells in medium containing no doxycycline. Specifically, immortalized megakaryocytes (SeV2-MKCL) obtained by the methods of 1. were washed twice with PBS(-), and suspended in the following medium at a seeding density of $1.0\times10^5$ cells/mL.

The medium was IMDM basic medium to which the following components had been added (final concentrations given).

| | |
|---|---|
| FBS | 15% |
| L-Glutamine (#25030-081 (Gibco)) | 2 mM |
| ITS (#41400-045 (Gibco)) | 100x dilution |
| MTG (monothioglycerol, #M6145-25ML (Sigma)) | 450 μM |
| Ascorbic acid (#A4544 (Sigma)) | 50 μg/mL |
| SCF (#193-15513 (Wako Pure Chemical Industries, Ltd)) | 50 ng/mL |
| TPO-like active substance | 200 ng/mL |
| ADAM inhibitor | 15 μM |
| SR1 | 750 nM |
| ROCK inhibitor | 5 μM |

The resulting immortalized megakaryocyte line suspension was added to a 125 mL shaker flask (medium 25 mL) and the stirring culture tank of a bioreactor (medium 700 mL). Platelets were produced by 3 to 9 days of culture under these culture conditions. A Biott Corporation BCP stirring culture tank (hereunder called the BCP) was used as the bioreactor.

In the BCP, 0.7 liters of the immortalized megakaryocyte line suspension was cultured in a 2-liter capacity culture tank or 0.5 liters were cultured in a 1-liter capacity culture tank. The stirring rate was 75 rpm. Stirring was performed using a rotary stirring blade. The specifications of the BCP were as follows: outer dimensions 300 (w)×905 (h)×500 (d) mm; culture tank liquid volume 0.5 to 10 L; spinner flask or vessel; lower magnet stirring system; rotational speed 10 to 140 rpm; temperature regulated to room temperature +10° C. to 45° C.; measurement control of stirring, temperature, pH, DO, level and feed.

The 125 mL shaker flask was shaking cultured at 100 rpm in a shaking culture incubator (AniCell, N-BIOTEK,) at 37° C., 5% $CO_2$.

3. Platelet Measurement

To measure the platelets produced by the method of 2, a culture supernatant sample was collected after 6 days of culture following termination of overexpression, stained with various antibodies, and analyzed by flow cytometry. The number of CD41a-positive CD42b-positive particles was given as the number of normal platelets, and the number of CD41a-positive CD42b-negative particles as the number of degraded platelets. The number of Annexin V-positive particles was given as the number of unusual platelets. The samples were stimulated with PMA or ADP/Thrombin, and the positive rates for PAC-1 and CD62p before and after stimulus were calculated as a measure of bioactivity.

The detailed measurement methods and results were as follows.

3-1. Platelet Measurement

To measure the normal platelets, degraded platelets and platelet bioactivity, 900 µL of diluted solution was added to a 1.5 mL microtube, and 100 µL of culture supernatant was added thereto and mixed. 200 µL of the diluted mixed culture supernatant was dispensed into a FACS tube, and stained by addition of the following labeled antibodies or protein. To measure unusual platelets, 100 µL of the culture supernatant was dispensed into a FACS tube, stained by addition of the following labeled antibodies or protein, diluted 5 times with Annexin V binding buffer (Becton, Dickinson and Company) immediately prior to flow cytometry analysis, and analyzed.

The antibodies used were as follows.
For measuring normal platelets and degraded platelets
  0.5 µL anti-CD41 antibody, APC label (303710 (BioLegend, Inc.))
  0.5 µL anti-CD42a antibody, PB label (48-0428-42 (eBioscience))
  0.5 µL anti-CD42b antibody, PE label (12-0428-42 (eBioscience))
For measuring platelet bioactivity
  0.5 µL anti-CD42a antibody, PB label (48-0428-42 (eBioscience))
  0.5 µL anti-CD42b antibody, PE label (12-0428-42 (eBioscience))
  0.5 µL anti-CD62p antibody, APC label (304910 (BioLegend, Inc.))
  10 µL anti-PAC-1 antibody, FITC label (303704 (Becton, Dickinson and Company))
For measuring numbers of unusual platelets
  0.5 µL anti-CD41 antibody, APC label (303710 (BioLegend, Inc.))
  0.5 µL anti-CD42a antibody, PB label (48-0428-42 (eBioscience))
  5 µL Annexin V, FITC label (556419 (Becton, Dickinson and Company))

3-2. Measuring Platelet Bioactivity

Platelets were stimulated at room temperature with 0.2 µM PMA (phorbol 12-myristate 13-acetate, #P1585-1MG (Sigma)) or 100 µM ADP (#A2754 (Sigma)) and 0.5 U/mL thrombin (Sigma). 30 minutes after stimulation they were measured with a Becton, Dickinson and Company FACSVerse flow cytometer.

The PAC-1-positive rate and CD62p-positive rate were measured before and after stimulation in the CD42a-positive platelet fraction, and subjected to comparative evaluation.

Figure 1:
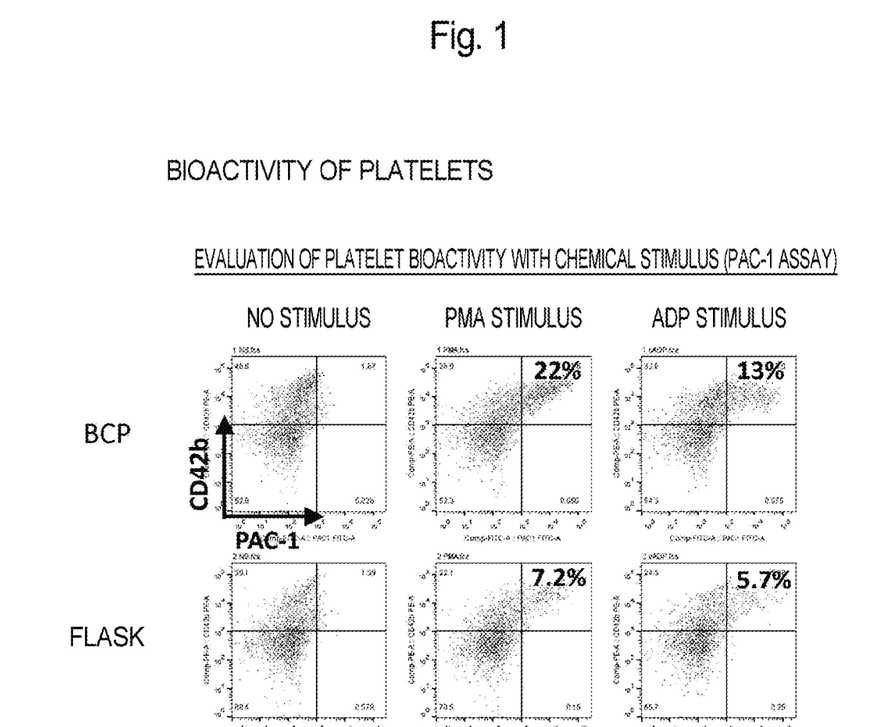
FIG. 1 shows the results of flow cytometry performed on platelets obtained by stirring culture or shaking culture of megakaryocytes, using anti-CD42b antibodies and anti-PAC-1 antibodies before and after stimulus with PMA or ADP.

The results are shown in FIG. 1. In the case of the BCP stirring culture, the MFI of the PAC-1-positive rate with PMA or ADP/thrombin stimulation was about two to three times that obtained under shaking culture conditions in a 125 mL shaker flask.

Figure 2:
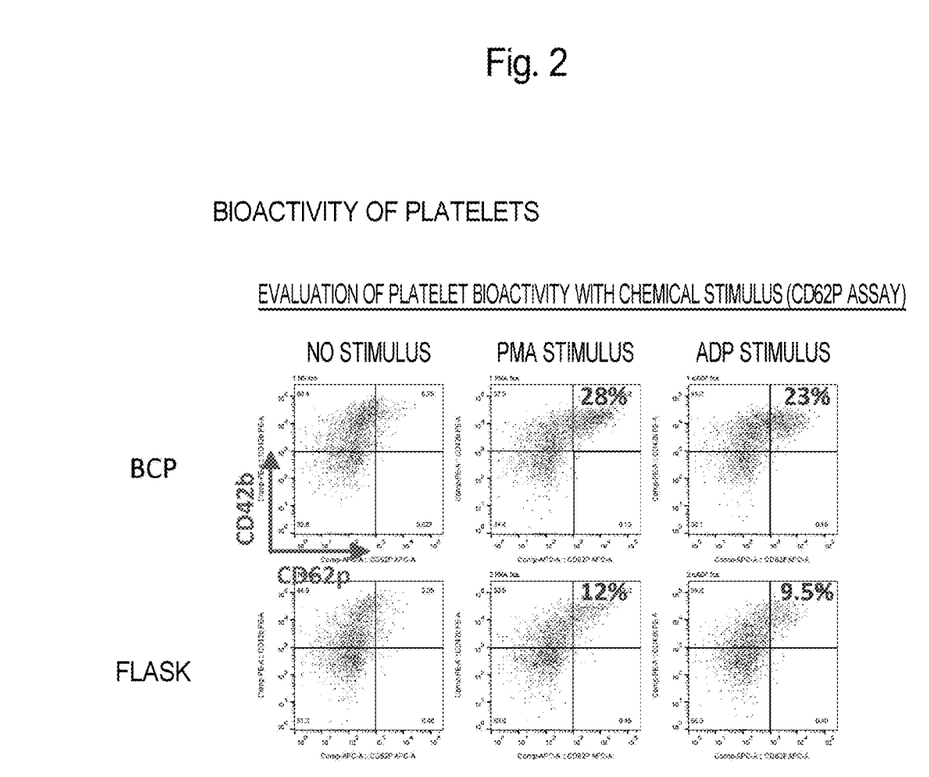
FIG. 2 shows the results of flow cytometry performed on platelets obtained by stirring culture or shaking culture of megakaryocytes, using anti-CD42b antibodies and anti-CD62p antibodies before and after stimulus with PMA or ADP.

Moreover, as shown in FIG. 2, in the case of the BCP stirring culture the CD62p positive rate was at least 2 times that obtained from a shaking culture in a shaker flask, indicating the platelets with strong bioactivity were obtained.

3-3. Measuring Platelet Degradation

Each treatment sample was analyzed by flow cytometry by the methods of 3-1. above, and the number of CD41a-positive CD42b-positive particles was calculated as the number of normal platelets and the number of CD41a-positive, CD42b-negative particles as the number of degraded platelets.

Figure 3:
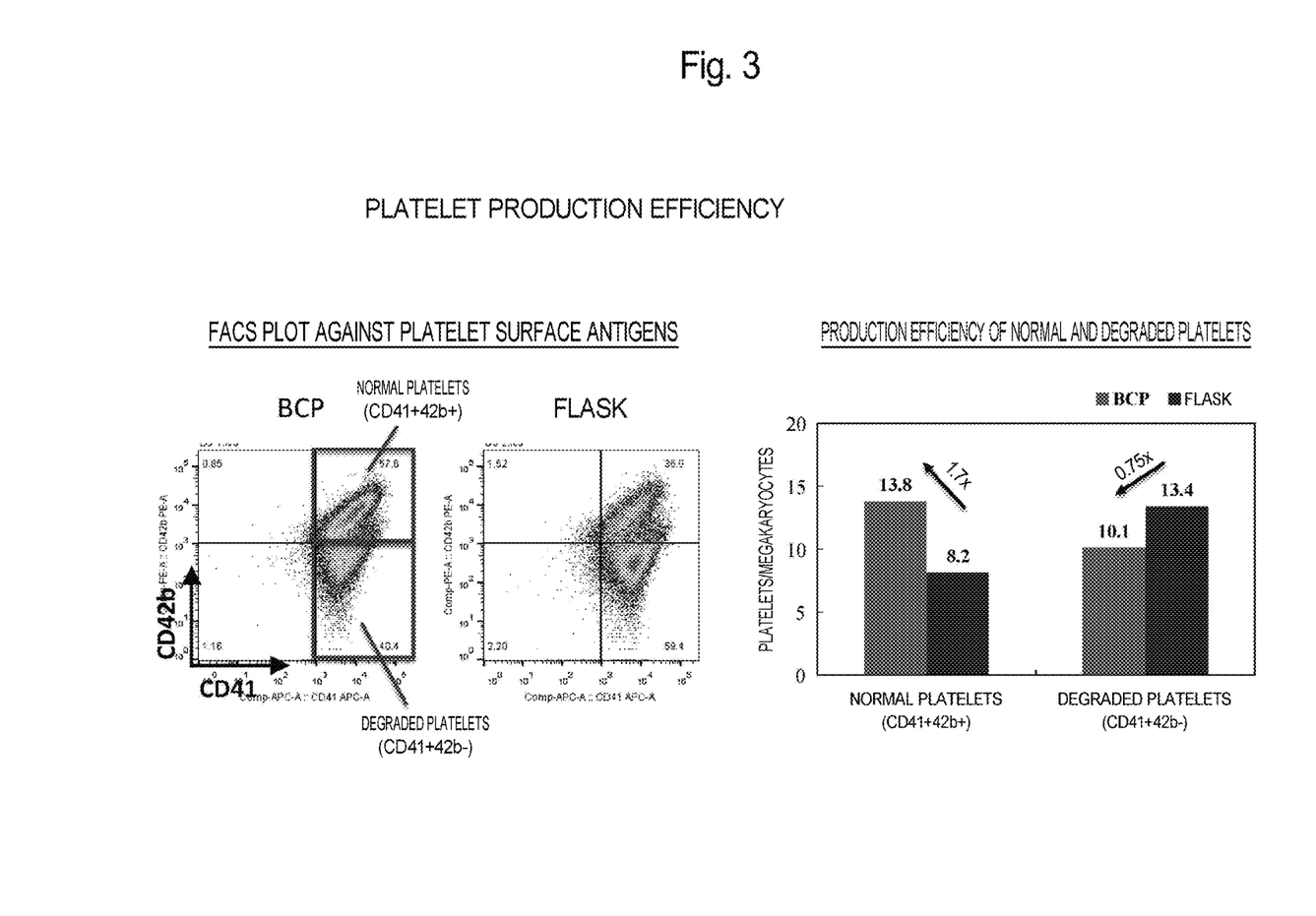
FIG. 3 shows the results of flow cytometry performed on platelets obtained by stirring culture or shaking culture of megakaryocytes, using anti-CD41a antibodies and anti-CD42b antibodies.

The results are shown in FIG. 3. The production efficiency of normal platelets in the BCP stirring culture was about 1.7 times that of the shaking culture. Furthermore, the number of degraded platelets in the BCP stirring culture was reduced to about 0.75 times that of the shaking culture.

3-4. Measuring Unusual Platelets

Figure 4:
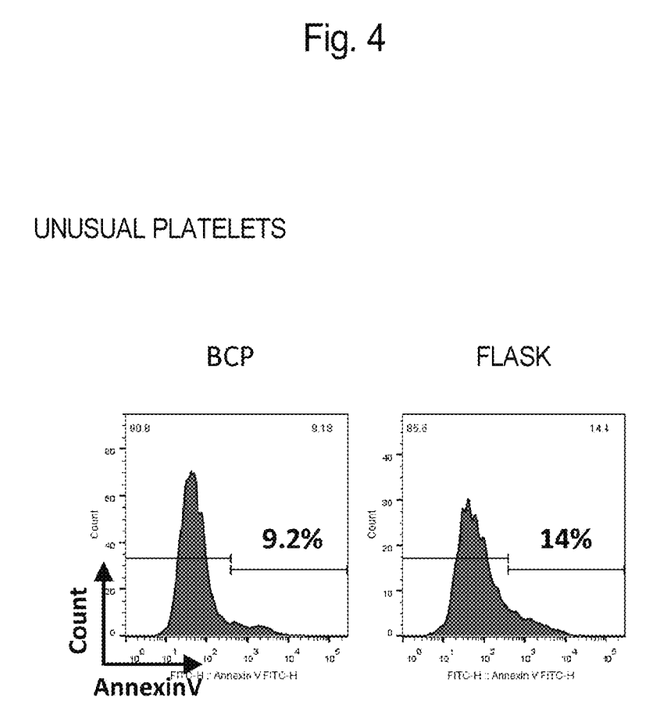
FIG. 4 shows the rate of Annexin V binding in platelets obtained by stirring culture or shaking culture of megakaryocytes as measured by flow cytometry.

Each treatment sample was analyzed by flow cytometry by the methods of 3-1. above, and the number of Annexin V-positive particles was given as the number of unusual platelets. The results are shown in FIG. 4. The number of unusual platelets in the BCP stirring culture was reduced to about 0.7 times that of the shaking culture.

4. Optimizing Culture Conditions

The stirring rotational speed of the BCP stirring culture incubator was altered, and differences in platelet production efficiency were measured. The stirring rotational speed was set at 100 rpm, 120 rpm or 140 rpm, and CD41a-positive CD42b-positive particles were measured with the results shown in FIG. 5.

Figure 5:
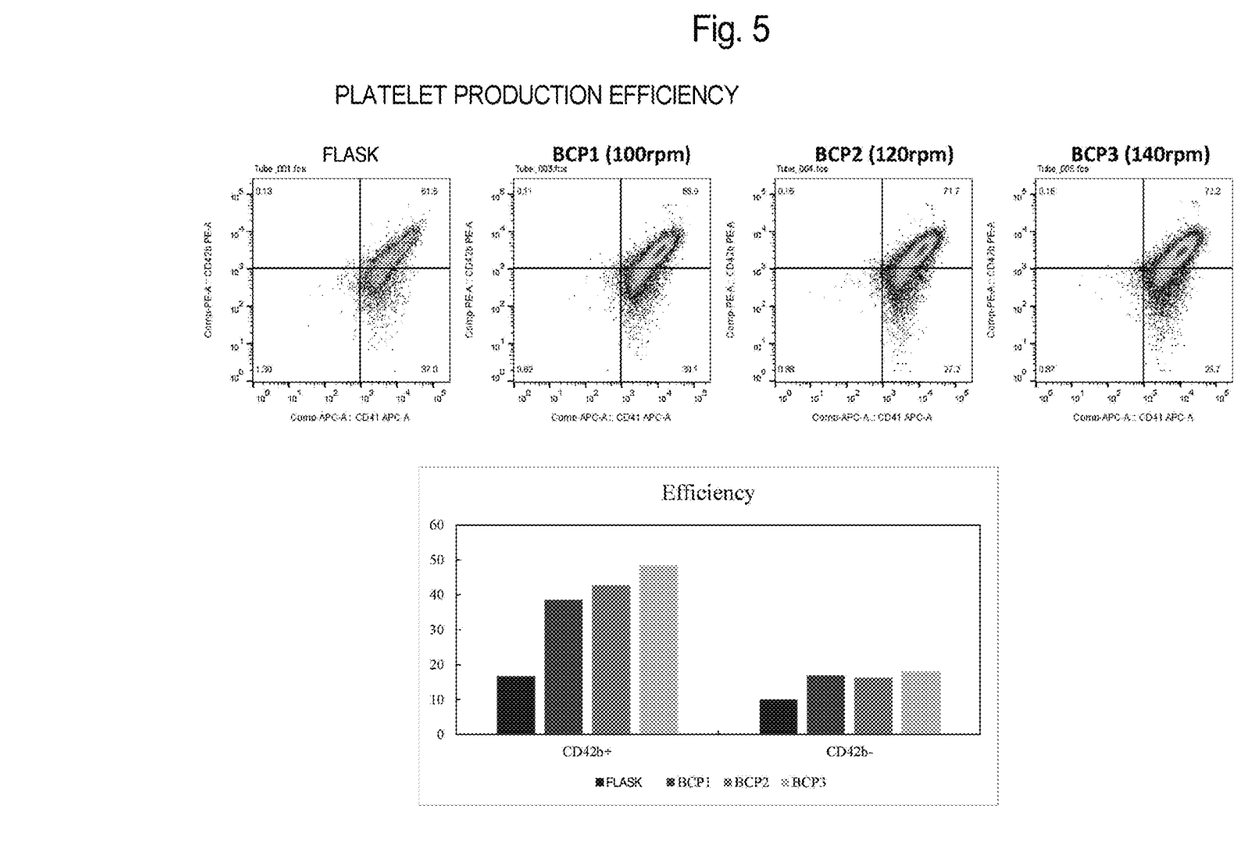
FIG. 5 shows the results of flow cytometry performed using anti-CD41a antibodies and anti-CD42b antibodies on platelets obtained by stirring culture at different rotational speeds.

Production of platelets (CD41a-positive CD42b-positive) was greatest at the highest rotational speed of 140 rpm.

INDUSTRIAL APPLICABILITY

Clearly, high-quality platelets that cannot be obtained with a shaking culture in a shaking flask can be obtained by the present invention. Thus, the present invention can contribute to achieving mass production of platelets at an industrial level.

What is claimed is:

1. A method for producing platelets, comprising
a step of culturing megakaryocytes in a culture solution in a culture vessel, wherein the culture solution is stirred with a stirring blade in the culture step.

2. The method according to claim 1, wherein the stirring blade is a flat-bladed turbine blade, a propeller blade, an arrowhead blade, a curved blade, or a one plane disk turbine blade.

3. The method according to claim 1, wherein the culture vessel is a sealed bioreactor.

4. The method according to claim 1, wherein the stirrer is rotated at a rotational speed of at least 50 rpm.

5. The method according to claim 1, wherein the megakaryocytes are cells obtained by overexpressing at least one gene selected from the group consisting of a cancer gene, a polycomb gene and an apoptosis suppression gene in undifferentiated cells of megakaryocytes, and then terminating the overexpression.

6. A method for producing a platelet preparation, comprising:
a step of producing platelets in megakaryocytes by the method according to claim 1 and collecting the platelets from a culture; and
a step of removing blood cell components other than platelets from the platelets.

7. A method for producing a blood preparation, comprising:
a step of manufacturing a platelet preparation by the method according to claim 6; and
a step of mixing this platelet preparation with other components to obtain a blood preparation.

* * * * *